United States Patent
Dedo

(10) Patent No.: US 8,535,346 B2
(45) Date of Patent: Sep. 17, 2013

(54) PRESSURE CUFF HOLDING DEVICE

(76) Inventor: Richard G. Dedo, Hillsborough, CA (US)

( * ) Notice: Subject to any disclaimer, the term of this patent is extended or adjusted under 35 U.S.C. 154(b) by 53 days.

(21) Appl. No.: 13/219,128

(22) Filed: Aug. 26, 2011

(65) Prior Publication Data

US 2012/0053616 A1    Mar. 1, 2012

Related U.S. Application Data

(60) Provisional application No. 61/378,715, filed on Aug. 31, 2010.

(51) Int. Cl.
*A61B 17/00*    (2006.01)
(52) U.S. Cl.
USPC .......................................... 606/203; 606/202

(58) Field of Classification Search
USPC ............. 606/202–203; 600/499; 229/117.23
See application file for complete search history.

(56) References Cited

U.S. PATENT DOCUMENTS

| | | |
|---|---|---|
| 2008/0051827 A1 | 2/2008 | McEwen |
| 2008/0132820 A1 | 6/2008 | Buckman et al. |
| 2008/0188889 A1* | 8/2008 | Dedo ............................ 606/203 |
| 2008/0189864 A1 | 8/2008 | Marguet et al. |
| 2009/0062843 A1 | 3/2009 | Heston |

* cited by examiner

*Primary Examiner* — Gregory Anderson
(74) *Attorney, Agent, or Firm* — Whyte Hirschboeck Dudek S.C.

(57) ABSTRACT

A constructed device for use maintaining an inflatable tourniquet cuff in place on a limb of a person, kits, and methods of using the device are provided. The construction of the cuff holding device prevents a blood pressure cuff or other tourniquet cuff from slipping out of position during use.

17 Claims, 5 Drawing Sheets

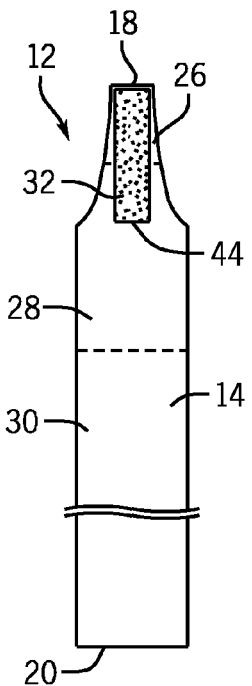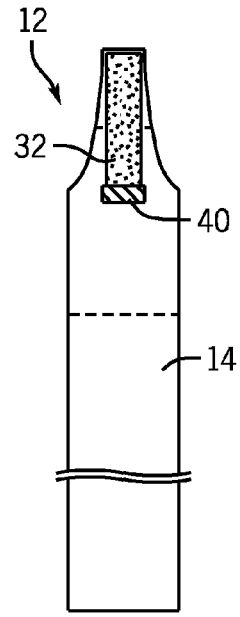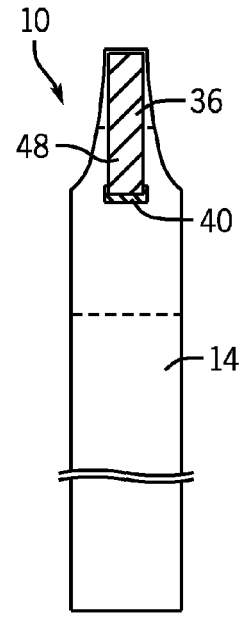
FIG. 3A  FIG. 3B  FIG. 3C
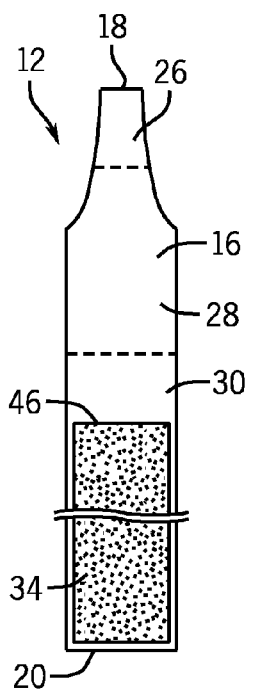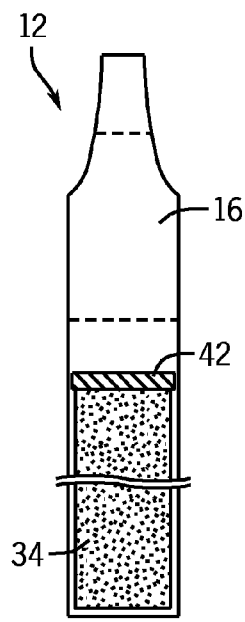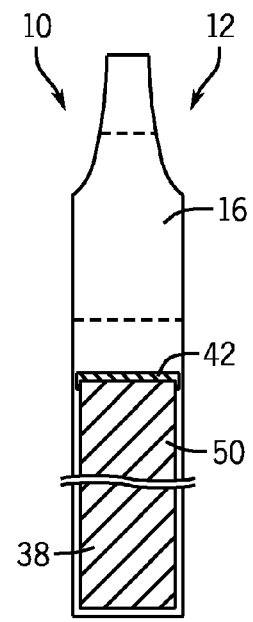
FIG. 3D  FIG. 3E  FIG. 3F

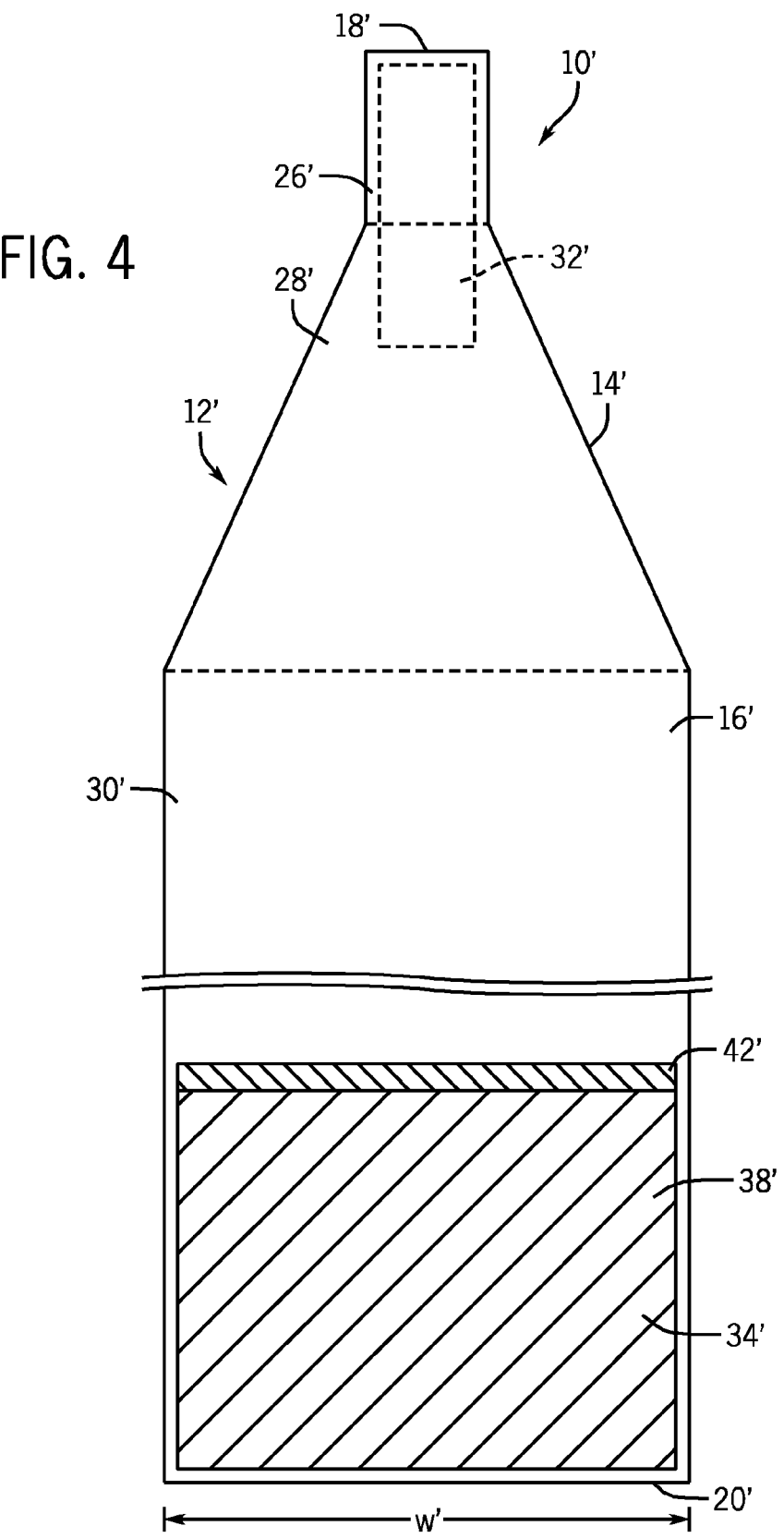

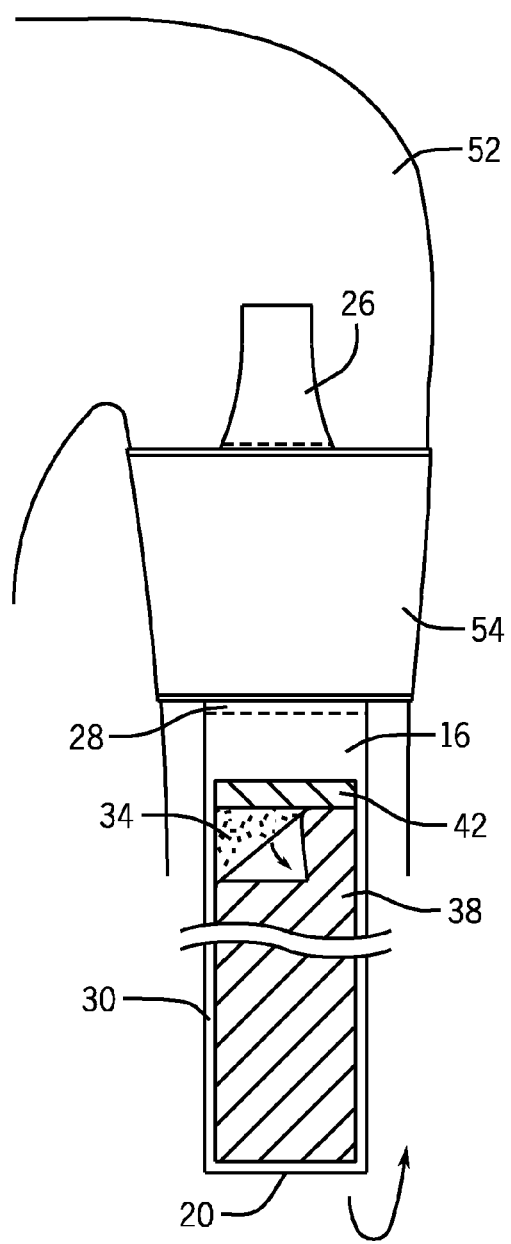
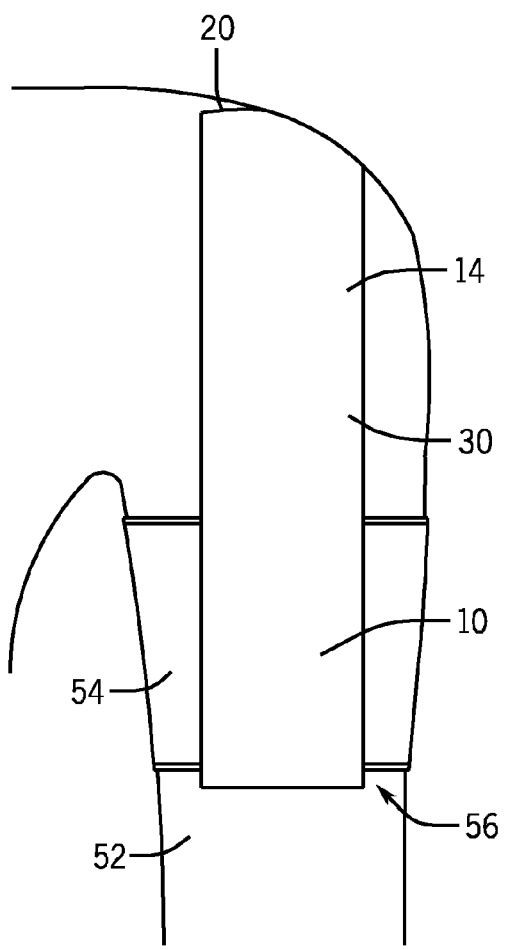
FIG. 5B
FIG. 5C

PRESSURE CUFF HOLDING DEVICE

CROSS REFERENCE TO RELATED APPLICATION

This application claims priority under 35 U.S.C. §119(e) to Provisional Patent Application Ser. No. 61/378,715, filed on Aug. 31, 2010, the entire disclosure of which is hereby incorporated by reference.

FIELD OF THE INVENTION

The present invention relates to a disposable device for use in the medical field, and more particularly to a device used in connection with blood pressure cuffs and other tourniquets, to hold the cuff in place on a limb during use.

BACKGROUND OF THE INVENTION

Tourniquet cuffs are used by orthopedists, anesthesiologists and other medical practitioners to stop the flow of blood through an artery by compression, and are typically placed proximally on an upper or lower extremity such as the upper arm or thigh, and occasionally in a more distal position such as on the calf. Inflatable tourniquet cuffs are commonly used in the medical field, and include bladders that are inflated by compressed air, producing enough compression to occlude the arterial flow. For an orthopedist or other surgeon who does extremity surgery, this achieves an avascular, or "non-bleeding," dry surgical field. By stopping the flow of blood into the extremity, surgery can be performed in that extremity distal to the tourniquet cuff without bleeding. With the artery occluded, no blood flows into the surgical field and the surgeon can perform surgery in what is temporarily a bloodless surgical field.

To completely stop the flow of blood, a tourniquet cuff should be applied as high as possible into the axilla or "armpit" in an upper extremity, or into the groin adjacent to the inguinal ligament located at the crease between the lower abdomen and the anterior, or front part of the top of the thigh. Such placement occludes the artery before it begins to divide into its branches, and provides a surgeon with a large operative field for elbow and knee surgery. A large area is needed in order to prep the skin adequately and to drape the area properly so that during surgery, if an incision needs to be extended, the surgeon does not need to cut through drapes to do so.

Tourniquet cuffs in the form of blood pressure cuffs, are also used by anesthesiologists to monitor blood pressure during surgical procedures, by nurses in intensive care units, by medical personnel in transitional care units, among others. A blood pressure cuff is often applied and left on for an extended time period, i.e., several days. The cuff is applied as high as possible on the upper extremity in order to more effectively occlude the artery before it branches and obtain a more accurate blood pressure measurement.

In use during a surgical procedure, a tourniquet cuff is applied with continuous pressure for an extended period of time. In the use of a blood pressure cuff during a surgical procedure or in an intensive care or cardiac care unit, the cuff is automatically and repeatedly inflated and deflated at about one to two minute intervals to monitor blood pressure, and can be left on for several days. This adds up to numerous compressions of the skin during a procedure or treatment period.

Tourniquet cuffs are commercially available and typically 2 to 6 inches wide for single bladder tourniquets and about 8 to 9 inches wide for double bladder tourniquets ("Bier blocks"). A blood pressure cuff about 4 inches wide is used most frequently by anesthesiologists. For an average size patient, a 4-inch wide tourniquet is used for upper extremity surgery, while a 4- to 6-inch wide tourniquet is typically applied to the thigh for surgeries on the lower extremities.

Tourniquet cuffs are generally supplied without padding, and some surgeons and anesthesiologists use a tourniquet cuff without padding underneath. However, this can result in injury to the skin caused by prolonged or intermittent pinching while the surgery is performed or when the blood pressure tourniquet cuff is inflated/deflated to monitor blood pressure. To avoid skin irritation and damage to the outer layers of the skin by the repeated compression, a soft padding material is often applied around the extremity under the cuff.

The use of tourniquet cuffs is problematic. The diameter or circumference of the upper arm and thigh decreases from the proximal end (i.e., shoulder, hip) to the distal end (i.e., elbow, knee). In most people, the upper arm and thigh are conically shaped like an ice cream cone, being wider at the top and narrowing toward the elbow or knee. This presents problems in maintaining a tourniquet cuff in a stationary position on the upper part of the arm or the upper part of the thigh. Oftentimes, a tourniquet cuff, with or without padding, tends to slip distally down the extremity during a procedure. This situation becomes more problematic as the weight of the person increases and the distal part of the extremity is proportionately smaller than the proximal part. In addition, a heavier patient tends to have looser skin and subcutaneous tissues, requiring a higher amount of compression to occlude the artery for surgery or to obtain blood pressure.

Slippage of a blood pressure cuff along a limb causes particular problems for anesthesiologists and surgeons. For surgical procedures, the tourniquet cuff is applied to the upper arm and inflated, blood pressure is recorded, and the cuff is then deflated. As this is repeated over an extended time during the procedure, the cuff slips distally and a different part of the extremity becomes compressed. This change in the location where the blood pressure measurements are taken can result in inaccurate readings.

There have also been numerous complaints about tourniquet slippage down the arm or thigh and causing problems with proper occlusion of the artery during surgical procedures. For a surgical operation performed on an elbow, knee, forearm, hand, calf or foot, as the tourniquet slips distally, compression decreases and compromises the surgical field with bleeding. In addition, the distal edge of the tourniquet is not sterile, and as the edge enters the surgical field, the potential for post-operative infection increases. There have also been problems with the tourniquet or cuff slipping off the underlying padding material onto the skin, resulting in blisters where the skin had been pinched.

One padding device, the Tournicuff® pressure cuff padding, described in U.S. Pat. No. 7,326,227 and U.S. Pat. No. 6,537,298 (Dedo), is designed as a wrap with an anti-slip surface against the skin to provide traction and reduce or preclude slippage of a tourniquet cuff during use. Although this device is effective as both padding and a holding device, it would be desirable to provide an alternate device for use in holding a tourniquet cuff in place on a limb during use.

SUMMARY OF THE INVENTION

The present invention provides a device designed to hold a tourniquet cuff in place on a limb and methods of its use.

In an embodiment of the invention, a non-inflatable device for holding an inflatable pressure cuff in an about stationary position on a limb of a person is provided, which comprises an elongate member having first and second sides, first and second opposing ends, a width and a length; a first section proximal to the first end, a third section proximal to the second end and a second section therebetween, each of said sections having a length; the first side of the elongate member bearing a first adhesive element at or near the first end and extending from the first section to the second section, and the second side of the elongate member bearing a second adhesive element at or near the second end; the length of the second section being at least a width of the inflatable pressure cuff, and the length of the third section being greater than the sum of the lengths of the first section and the second section and sufficient to allow the third section to be folded over a pressure cuff situated on said second section when said pressure cuff is inflated and to position the second end beyond the first end of the elongate member.

In use, the cuff holding device is applied to a limb of a person by attaching the first adhesive element to the limb such that the second section of the elongate member is positioned for receiving the tourniquet cuff thereon, the tourniquet cuff is mounted onto the second section of the device and secured around the limb; and the third section of the elongate member is folded over the tourniquet cuff and the second adhesive element is attached to the limb.

The cuff holding device can be provided as part of a kit comprising in association the device packaged with directions for applying the device and a tourniquet cuff to a limb of a person, optionally in combination with a tourniquet cuff and/or other items such as those used in the application of a tourniquet cuff.

BRIEF DESCRIPTION OF THE DRAWINGS

Preferred embodiments of the invention are described below with reference to the following accompanying drawings, which are for illustrative purposes only. Throughout the following views, the reference numerals will be used in the drawings, and the same reference numerals will be used throughout the several views and in the description to indicate the same or like parts.

FIG. 3A-3F illustrates sequential processing steps showing fabrication of the device shown in FIGS. 1A-1B, according to an embodiment of a method of the invention.

FIG. 4 is a plan view of the second side of another embodiment of a pressure cuff holding device according to the invention.

FIGS. 5A-5C are views of the device of FIGS. 1A-1B at sequential steps of applying the device and a tourniquet cuff onto the upper arm of a person.

DETAILED DESCRIPTION

Figure 1A:
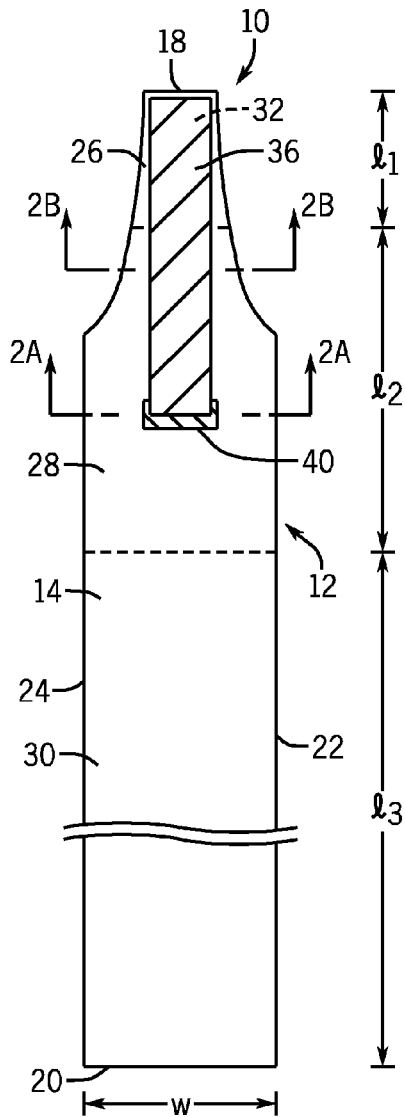
FIG. 1A is a plan view of a first side of an embodiment of a device for holding a pressure cuff according to the invention.

The present invention encompasses a pressure cuff holding device for use with a tourniquet, and methods for making and using the pressure cuff holding device. The pressure cuff holding device is a non-inflatable device for holding an inflatable pressure cuff in an about stationary position on a limb of a person.

The pressure cuff holding device of the invention can be used in conjunction with tourniquet cuffs that are applied with or without padding. The pressure cuff holding device can be used, for example, in conjunction with a padding device such as those described in U.S. Pat. No. 7,326,227 and U.S. Pat. No. 6,537,298 (Dedo), to enhance or augment the holding strength of the two devices.

As used herein, the term "upper extremity" refers to the "arm" of a person including the shoulder, arm, elbow, forearm, wrist and hand. The term "lower extremity" refers to the "leg" of the person including the hip, thigh, knee, calf, ankle and foot.

An embodiment of a pressure cuff holding device 10 of the present invention is described with reference to FIGS. 1A-1B. As shown, the cuff holding device 10 is structured as an elongate member 12 having a first side 14 (FIG. 1A) and a second side 16 (FIG. 1B), opposing first and second ends 18, 20, and opposing first and second side edges 22, 24, with an overall width (w) and length (l).

The elongate member 12 defines a first section 26 proximal to the first end 18, a second (intermediate) section 28, and a third section 30 proximal to the second end 20, each of the sections having a length ($l_1$, $l_2$, $l_3$). In the use of the device 10, an inflatable pressure cuff is positioned on the second (intermediate) section 28 (shown in FIG. 4B) which has a length ($l_2$) that is at least the width of the inflatable pressure cuff. Pressure cuffs vary in width and are generally available in widths of 2, 4 or 6 inches. Dual bladder ("Bier blocks") and other specialized tourniquet cuffs can be, for example, 8 to 9 inches in width. The elongate member 12 can include indicia such as lines (as shown) or arrows to delineate the second section 28 where the pressure cuff would be placed.

The length ($l_3$) of the third section 30 is greater than the sum of the lengths ($l_1+l_2$) of the first section 26 and the second (intermediate) section 28, and is sufficiently long such that the third section 30 can be folded over the pressure cuff situated on the intermediate section and in an inflated or pressurized state, and the second end 20 of the elongate member 12 positioned beyond the first end 18 of the elongate member onto the limb of the person. Preferably, the length ($l_3$) of the third section 30 is such that, when the third section is folded over a tourniquet positioned on the device, the second end 20 of the device extends generally about 7-10 inches or more beyond the second section 28 and the upper edge of the tourniquet cuff.

Although the size of the elongate member 12 can vary, exemplary size dimensions include an overall width (w) of about 3-6 inches or more and an overall length ($l=l_1+l_2+l_3$) of about 20-28 inches, with the length ($l_1$) of the first section 26 at about 3-4 inches, the length ($l_2$) of the second section 28 at about 4-8 inches, and the length ($l_3$) of the third section 30 at about 13-16 inches. As a non-limiting example, the elongate member 12 can have a width (w) of about 3 inches, an overall length of about 20 inches, a length ($l_1$) of the first section 26 at about 3 inches, a length ($l_2$) of the second section 28 at about 5 inches, and a length ($l_3$) of the third section 30 at about 12 inches.

Figure 1B:
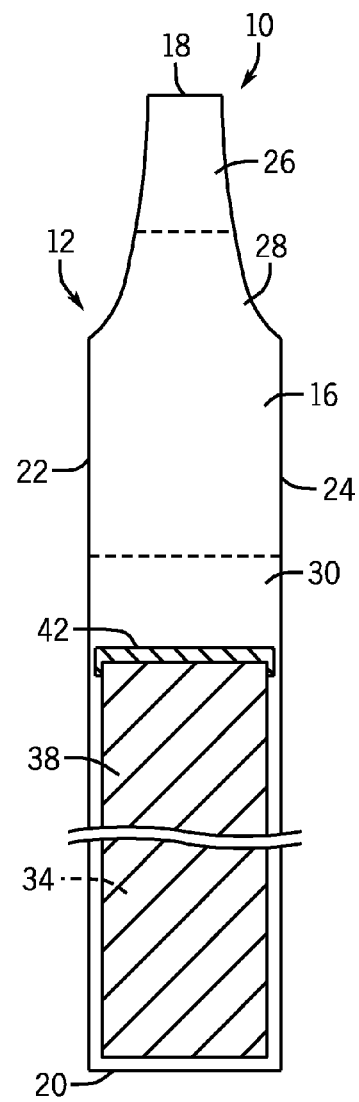
FIG. 1B is a plan view of the reverse side of the device shown in FIG. 1A.
Figure 2A:
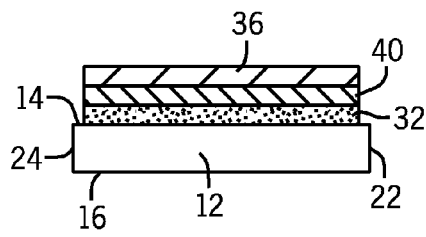
FIGS. 2A-2B are cross-sectional, side elevational views of the device shown in FIGS. 1A-1B, taken along lines 2A-2A and 2B-2B, respectively.
Figure 2B:
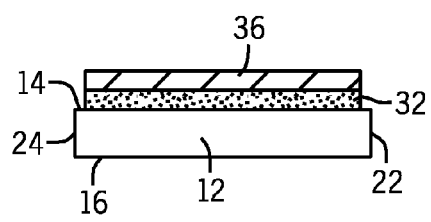

In preferred embodiments, the elongate member 12 is formed from a unitary sheet of material, as shown in FIGS. 1A-1B. The elongate member can be in a rectangular shape (as shown) or other shape (e.g., elongated oval, etc.), and can be structured as depicted with a tapered or narrower first end 18.

The elongate member 12 can be manufactured from any suitably compliant, natural or synthetic (man-made) material including but not limited to, paper, scrim reinforced tissue or other reinforced scrim material, crepe, cloth, terry cloth, cheesecloth, plastic (polymer film), and the like, and combinations thereof. Also useful are non-woven fabrics such as felt (carded non-woven) made from polyester, rayon or other fiber, or absorbent web (airlaid non-woven) made from wood pulp or synthetic fibers typically used for diapers, baby wipes, sanitary towels, drapes and gowns, among other products. The elongate member can be fabricated as a laminate, for example, a laminate of tissue and a non-woven or woven substrate, a laminate of a polymer film (e.g., polyethylene) backing and non-woven or woven substrate material such as a tissue/poly laminate similar to that used for dental bibs and table coverings, a polyurethane foam-polymer film laminate (thermo- or adhesively laminated) similar to that used for EMS blankets, and the like. Preferably, the elongate member is composed of a material that is porous (breathable) to pass moisture, vapor and air.

A preferred material comprises a lightweight conformable scrim reinforced material that allows the device to readily flex. Scrim reinforced materials are well known and widely used, and comprise threads or filaments. Preferably, the scrim fibers or strands are embedded or partially embedded in the material, and are preferably interwoven at about right angles in an open mesh web or grid. Suitable scrims can be made from paper, knits, wovens, non-wovens and extruded porous sheets such as materials available from Conweb, Minneapolis, Minn. Examples of suitable scrim filaments include fiberglass and ceramic fibers, and fibers made of polyester, polyethylene and other polyolefins, polyacrylate, rayon, cotton, hemp, jute, natural rubber, polyurethane, and blends thereof. Scrim materials are also described, for example, in U.S. Pat. No. 6,027,465, U.S. Pat. No. 6,100,206, and U.S. Pat. No. 6,132,835 (Scholz et al., 3-M Company), the disclosures of which are herein incorporated by reference.

The first side 14 of the elongate member 12 bears a first adhesive element 32 at or near the first end 18 for initial attachment of the device 10 to the limb of the person. The second side 16 of the elongate member 12 bears a second adhesive element 34 at or near the second end 20.

Adhesive material can be applied in the form of a solid strip or band, intermittent lines, dots, discrete or disconnected segments, or other form. The adhesive material of elements 32, 34 is sufficiently adherent to secure the first and second ends 18, 20 of the elongate member 12 to the limb and maintain the device 10 and a tourniquet cuff in a "substantially stationary position" on the limb during use, that is, a minimal amount of slippage of the tourniquet cuff of up to about one-inch from its original position on the limb. The adhesive material is preferably a biocompatible and hypoallergenic adhesive material that is adherable to skin but will release from the skin with minimal trauma. Such adhesives are well known in the art and commercially available. Useful adhesives include, for example, acrylic adhesives that are used in surgical applications where reduced skin trauma is required. Preferably, the adhesive is a pressure-sensitive adhesive substance.

In other embodiments, the adhesive elements 32, 34 can comprise a frictionally adhesive material having anti-slip properties, for example, latex rubber, silicon rubber, or foamed polyvinyl chloride, with a typical thickness of about 0.001 to about 0.5 mm. Such materials are described for example, in connection with anti-slip socks used in hospitals, hotels, and the like, non-slip garments, and non-slip mats, such as in U.S. Pat. No. 6,332,825 (Henrickson), U.S. Pat. No. 6,041,443 (Pas et al.), U.S. Pat. No. 6,022,617 (Calkins), and U.S. Pat. No. 5,901,706 (Griesbach et al.), the disclosures of which are incorporated by reference herein. Such anti-slip material can be applied as a coating to the sides 14, 16 of the elongate member 12.

The adhesive elements 32, 34 are covered by a releasably attachable release or slip sheet 36, 38, as known and used in the art. An example of a useful slip material is a polycoated paper (coated with high density, moderate density, or low density polyethylene). In preferred embodiments, to facilitate removal (e.g., peeling off) of the release sheets from the adhesive elements, a tab section 40, 42 is applied over an end 44, 46 of the adhesive elements 32, 34 with the end 48, 50 of the release sheet extending over the tab section (as depicted in FIGS. 3A-3F). The tab sections 40, 42 can be composed of the same material used for the release sheets or other suitable material. The release sheets 36, 38 can be peeled off just prior to applying the device 10 to the limb.

In the embodiment shown in FIG. 1A, the first adhesive element 32 is in the form of a band that extends from the first end 18 into the second section 28 of the elongate member (FIG. 3A). It is desirable that the second section 28 includes at least a portion of the adhesive element 32 whereby pressure from the inflating cuff (mounted within the second section 28 on the second side 16 of the device) enhances the adherence of the underlying adhesive element 32 to maintain the device 10 (and the cuff) in place on the limb.

In some embodiments, a liquid-repellent material can been bonded to one or both sides of the elongate member 12 (not shown). Suitable liquid-repellent materials include those that repel and/or are impermeable or impervious to liquids, including, for example, polyethylene or other plastic sheeting material. The adhesive elements would then be applied to the liquid-repellent material.

In preferred embodiments, the cuff holding device is fabricated without padding. In some embodiments, where desired, a padding material (not shown) can be bonded to the second side 16 of the elongate member 12 within the second section 28 for placement under the tourniquet cuff. Such padding material can be a porous or non-porous material, and a natural or synthetic fiber material. Examples of padding materials include cast padding that is made from cotton, nylon, rayon, acrylic, polyester or other like materials and blends, paper materials, a scrim-reinforced materials, and foamed materials such as a polyurethane foam or other material having memory that will return to its pre-compressed shape after being compressed.

An embodiment of a process for fabricating the device 10 is depicted in FIGS. 3A-3F. Shown in FIG. 3A is the first side 14 of the elongate member 12, which has been formed to the desired size, shape and length. As depicted in FIG. 3A, an adhesive material 32 is applied to the first section 26 and part of the second section 28. A tab section 40 is then applied to an end 44 of the adhesive element 32 (FIG. 3B), and a release sheet 36 is then applied to the adhesive element 32 with the end 48 of the release sheet 36 extended over the tab section 40 (FIG. 3C), which provides ready removal of the release sheet. Similarly, as depicted in FIG. 3D, an adhesive material is applied to the third section 30 to form adhesive element 34, a tab element 42 applied to the end 46 of the adhesive element 34 (FIG. 3E), and a release sheet 38 applied to the adhesive element 34 with the end 50 of the release sheet over the tab element 42.

The device 10 can be fabricated in a continuous roll either end-to-end or side-to-side, and cut from the roll, or perforations can be provided at each end 18, 20 or along each side edge 22, 24 between each device for ready separation.

Another embodiment of a cuff holding device 12' according to the invention is illustrated in FIG. 4. The device 12' features a tapered second section 28' and a wider end 20' at the third section 30' with a wider adhesive element 34' than the holding device 12 depicted in FIGS. 1A-1B, to enhance and strengthen the attachment of the third section 30' to the limb.

As shown, second section 28' widens toward the third section 30' to a width (w') for the second and third sections 28', 30' of the elongate member 12'. As a non-limiting example, the end 20' of the device 12' can have a width (w') of about 6-8 inches.

Figure 5A:
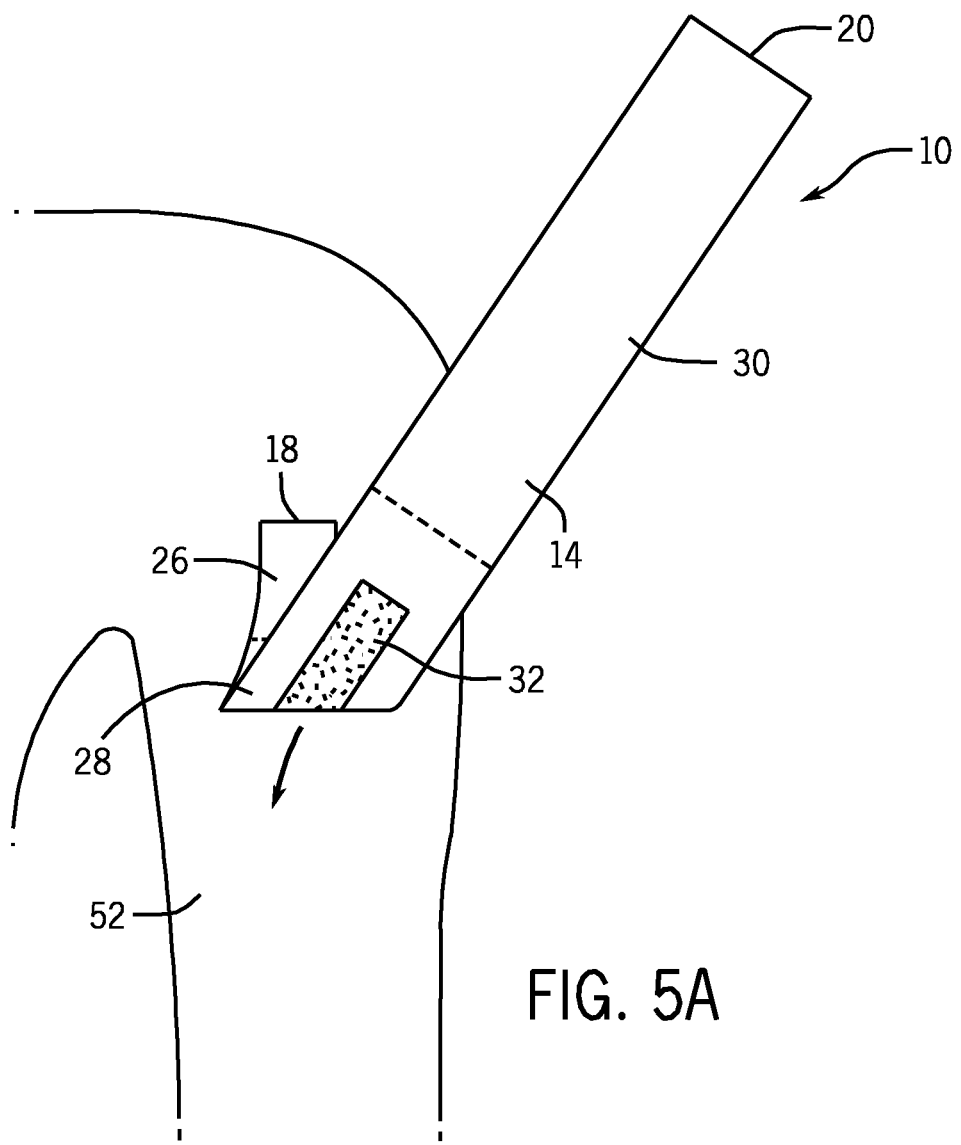

Referring now to FIGS. 5A-5C, the cuff holding device 10 can then be applied to a limb, shown as arm 52. The release sheet 36 is removed to expose the adhesive element 32 on the first side 14 of the cuff holding device 10 and, as shown in FIG. 5A, with the first side 14 facing the limb and the first end 18 oriented near the shoulder, the adhesive element 32 is applied to the upper arm such that the second section 28 is positioned in the location for placement of the tourniquet cuff 54. The device 10 can be placed on the front of the limb (as shown), on the lateral aspect of the limb, and/or posteriorly at the back of the limb. Two or more devices 10 can be applied at different positions on the limb and used in combination to hold the tourniquet cuff in place. Then, as shown in FIG. 5B, the tourniquet cuff 54 is positioned over the second section 28 of the holding device 10 and wrapped around and secured to the upper arm 52. Although not shown, a padding layer can be positioned on the second section 28 of the holding device under the tourniquet cuff 54 to provide cushioning.

As depicted in FIG. 5B, the release sheet 38 is then removed (arrow) to expose the adhesive element 34 on the second side 16 of the device. The second end 20 of the device is then brought upwardly (arrow) and folded over the tourniquet 54 and, as illustrated in FIG. 5C, the adhesive element 34 is adhered to the upper arm at or near the shoulder area. To accommodate the inflation of the tourniquet cuff 54, it is desirable that a gap 56 is provided between the edge of the (uninflated) tourniquet cuff and the fold of the third section 30 and the third section is not taut over the uninflated tourniquet cuff. This will prevent a premature disengagement of the adhesive element 34 from limb. With the cuff holding device 10 securely positioned over the tourniquet cuff 54 and adhered to the limb 52 of the user, the tourniquet cuff 54 can be inflated and deflated with substantially no or minimal slippage down the limb of the person.

Components can be separately packaged and combined within a packaging as a kit for providing the pressure cuff device 10 according to the invention. For example, an embodiment of a kit can include the pressure cuff device 10 contained within packaging (e.g., sterile bag), optionally packaged with one or more other items such as additional adhesive elements, a tourniquet cuff, gloves, container(s) of pharmaceutical composition(s), sterilizing wash(es), etc., a drape sheet, and instructions and directions for use of the cuff holding device and other components of the kit.

The present pressure cuff holding device advantageously holds a blood pressure cuff or other tourniquet cuff in place on a limb and prevents it from slipping down the limb during use. The configuration and placement of the device 10 of the invention with one portion (i.e., second section 28) positioned underneath the tourniquet cuff and another portion (i.e., third section 30) folded upwards and over the tourniquet cuff, and one adhesive element 32 situated underneath the tourniquet cuff during inflation of the cuff and a second adhesive element 34 adhering the second end 20 of the device to the location on the limb above the tourniquet cuff reduces or precludes slippage of the tourniquet cuff (54) during use.

The invention has been described by reference to detailed examples and methodologies. These examples are not meant to limit the scope of the invention. It should be understood that variations and modifications may be made while remaining within the spirit and scope of the invention, and the invention is not to be construed as limited to the specific embodiments shown in the drawings.

What is claimed:

1. A non-inflatable device for holding an inflatable pressure cuff in an about stationary position on a limb of a person, the device comprising:

an elongate member having first and second sides with a width (w) therebetween, first and second opposing ends with a length therebetween, a first section extending for a length ($l_1$) from the first end, a third section extending for a length ($l_3$) from the second end and a second section therebetween having a length ($l_2$), and the width (w) being wider at the second end than at the first end;

the first side of the elongate member bearing a first adhesive element at or near the first end and extending from the first section onto at least a part of the second section, and the second side of the elongate member bearing a second adhesive element at or near the second end;

the length ($l_2$) of the second section being at least a width of the inflatable pressure cuff, and the length ($l_3$) of the third section being greater than the sum of the lengths ($l_1+l_2$) of the first section and the second section and sufficient to allow the third section to be folded over a pressure cuff situated on said second section when said pressure cuff is inflated and to position the second end beyond the first end of the elongate member, and the width (w) of the elongate member being less than a circumference of the limb.

2. The device of claim 1, wherein in a folded condition, the second end of the elongate member extends at least about seven (7) inches beyond the second section of the elongate member.

3. The device of claim 1, further comprising a slip sheet releasably attached to said adhesive elements.

4. The device of claim 1, wherein the elongate member is a continuous sheet.

5. The device of claim 1, wherein the elongate member is composed of a scrim reinforced material.

6. The device of claim 1, wherein the length of the elongate member is greater than the width (w).

7. The device of claim 1, wherein the width (w) of the elongate member is up to about eight inches.

8. The device of claim 7, wherein the width (w) of the elongate member is about 3 to about 8 inches.

9. The device of claim 1, wherein the first section has a width less than the width of the second section.

10. The device of claim 1, wherein the first end is tapered.

11. The device of claim 1, wherein the second section is tapered.

12. A kit comprising in association:
a device according to claim 1; and
directions for applying the device and a tourniquet cuff to a limb of a person.

13. The kit of claim 12, further comprising a tourniquet cuff.

14. A method of applying a tourniquet cuff to a limb of a person, comprising:
applying the device according to claim 1 to said limb by attaching the first adhesive element to said limb such that the second section of the elongate member is positioned for receiving the tourniquet cuff thereon;
securing the tourniquet cuff onto the second section of the device and around the limb;
folding the third section of the elongate member over the tourniquet cuff and attaching the second adhesive element to the limb.

15. The method of claim 14, wherein the third section of the elongate member is folded over the tourniquet cuff to provide a gap therebetween.

16. The method of claim 14, wherein upon inflation of the pressure cuff, the second adhesive element remains attached to the limb and the tourniquet cuff is held substantially in place with minimal or no slippage on the limb.

17. A method of applying an inflatable pressure cuff to a limb of a person, comprising:
  applying a non-inflatable device to said limb, the device comprising:
    an elongate member having first and second sides, first and second opposing ends, a width and a length; a first section proximal to the first end, a third section proximal to the second end and a second section therebetween, each of said sections having a length;
    the first side of the elongate member bearing a first adhesive element at or near the first end and extending from the first section to the second section, and the second side of the elongate member bearing a second adhesive element at or near the second end;
    the length of the second section being at least a width of the pressure cuff, and the length of the third section being greater than the sum of the lengths of the first section and the second section and sufficient to allow the third section to be folded over a pressure cuff situated on said second section when said pressure cuff is inflated and to position the second end beyond the first end of the elongate member,
  wherein the device is applied by attaching the first adhesive element to said limb such that the second section of the elongate member is positioned for receiving the pressure cuff thereon;
  securing the pressure cuff onto the second section of the device and around the limb; and
  folding the third section of the elongate member over the pressure cuff and attaching the second adhesive element to the limb.

* * * * *